United States Patent [19]
Akiyama

[11] Patent Number: 5,355,186
[45] Date of Patent: Oct. 11, 1994

[54] OPHTHALMIC MEASUREMENT APPARATUS

[75] Inventor: Koichi Akiyama, Sagamihara, Japan
[73] Assignee: Kowa Company Ltd., Japan
[21] Appl. No.: 846,568
[22] Filed: Mar. 5, 1992

[30] Foreign Application Priority Data

May 14, 1991 [JP] Japan .................. 3-107710

[51] Int. Cl.⁵ .................. A61B 3/10
[52] U.S. Cl. .................. 351/215; 351/221
[58] Field of Search .............. 351/205, 210, 213, 215, 351/221, 207, 233; 606/4, 7

[56] References Cited

U.S. PATENT DOCUMENTS

| | | | |
|---|---|---|---|
| 4,346,991 | 8/1982 | Gardner et al. | 351/221 |
| 4,367,019 | 1/1983 | Kitao et al. | 351/205 |
| 4,541,697 | 9/1985 | Remijan | 351/211 |
| 4,877,321 | 10/1989 | Ichihashi et al. | 351/221 |
| 4,917,486 | 4/1990 | Raven et al. | 351/221 |
| 4,988,184 | 1/1991 | Akiyama | 351/221 |
| 4,991,954 | 2/1991 | Akiyama | 351/221 |
| 5,000,562 | 3/1991 | Ichihashi et al. | 351/221 |

Primary Examiner—Ricky D. Shafer
Attorney, Agent, or Firm—Bruce L. Adams; Van C. Wilks

[57] ABSTRACT

An ophthalmic measurement apparatus comprises a laser beam projection section for projecting into an eye a linearly polarized laser light beam emitted by a laser source, and a light receiving section provided with a photosensor for detecting laser light scattering from within the eye. An angle of the optical axes formed by both the sections with respect to the eye is set to be substantially ninety degrees. The polarization direction of the laser beam from the laser beam projection section is made variable in such a way that, during alignment, the polarization direction is set substantially perpendicular to a plane that includes the optical axes of both the sections, and during measurement it is set in a direction that is substantially in the plane. This arrangement makes it possible to cut noise components caused by light scattered by flares which are much smaller than the wavelength of the light.

10 Claims, 6 Drawing Sheets

OPHTHALMIC MEASUREMENT APPARATUS

BACKGROUND OF THE INVENTION

The present invention relates to an ophthalmic measurement apparatus, particularly to an ophthalmic measurement apparatus that irradiates the interior of an eye with a beam of substantially visible-region laser light, and uses the light scattered from the interior of the eye to perform specific measurements.

Measurement of floating cells in the anterior chamber is of critical importance when diagnosing ophthalmic inflammations, especially malfunctions of the blood-aqueous barrier and uveitis. Conventionally, a slit lamp microscope is often used for this, with grading being accomplished via the naked eye. A photographic measuring method has also been developed to provide quantitative measurements. However, no method has yet been perfected that is readily applicable to clinical examinations.

A problem with the conventional method of naked-eye measurement is the fact that as standards of judgment vary from person to person, the data thus obtained lacks reliability. One solution in recent years has been to develop ophthalmic measurement systems whereby a beam of laser light is projected into the eye and the light scattering from the eye is detected and subjected to quantitative analysis.

JP-A-64 (1989)-2623 (corresponding to U.S. Pat. No. 5,000,562) discloses an example of a method of measuring floating cells in the anterior chamber by irradiating the eye with a beam of laser light, and then measuring the light scattering from the eye. Similarly, JP-A-63 (1988) -288134 (corresponding to U.S. Pat. No. 4,991,954) discloses an example of a technique of measuring the concentration of plasma proteins (hereinafter also referred to as "flares") in the anterior chamber.

However, in the anterior chamber of a normal eye there are so few floating cells that, depending on the degree of inflammation, it may only be possible to count them using a slit lamp microscope. Therefore in cases in which the volume of the measurement space is small and there are few cells, sometimes there will be cells in the measurement space and sometimes there will be no cells.

This means that even though there may be cells in the overall anterior chamber, a cell count of zero could be obtained if there happens to be no cells in the measurement space. When this happens, the discrepancy between such a cell count and what has been seen by a visual observation has caused some examiners to distrust the system apparatus. It is preferable, therefore, to increase the size of the measurement space, which is defined by the scanning width of the laser beam used to scan the eye.

On the other hand, the presence of large numbers of cells signifies a higher degree of inflammation, in which case there will also be a higher concentration of flares. Light scattered by these flares increases the intensity of the scattered light impinging on the photosensor component of the ophthalmic measurement apparatus. Moreover, enlarging the measurement space will cause a further increase in this received light intensity level.

The flare components form a background noise component, and in received light the effect of a high level of such flare components is to bury cell signal components. The result is a loss of reliability with respect to measured values caused by an inability to differentiate between cell signal components and noise components.

SUMMARY OF THE INVENTION

An object of the present invention is therefore to provide an ophthalmic measurement apparatus that performs prescribed measurements on a target eye by projecting a beam of laser light into the interior of the eye and detecting the light scattering therefrom, and in the process cuts noise components caused by light scattered by flares, thereby making it possible to ensure that accurate measurements are obtained even when there is intense inflammation in the eye.

In accordance with the present invention, this object is attained by an ophthalmic measurement apparatus of the type described above, comprising a laser beam projection section for projecting into an eye a linearly polarized laser light beam emitted by a laser source, and a light receiving section provided with a photosensor for detecting laser light scattering from within the eye. An angle of the optical axes formed by the laser beam projection section and light receiving section with respect to the eye to be examined is set to be substantially ninety degrees. In this arrangement, a polarization direction of the laser beam from the laser beam projection section is made variable in such a way that, during alignment of the eye with the optical system of the apparatus, the polarization direction is set substantially perpendicular to a plane that includes the optical axes of the laser beam projection section and light receiving section, and during measurement operations it is set in a direction that is substantially in the plane.

With this arrangement, when measurements are being conducted, the direction of polarization of the laser beam impinging on the eye is substantially along a plane that includes the optical axes of the projection and receiving sections. Therefore, light that is scattered substantially at ninety degrees to the side that are much smaller than the wavelength of the light, is highly attenuated (Rayleigh scattering) . In contrast, as the size of cells is in the order of several tens of micrometers, scattered light from cells (Mie scattering) is little affected by the direction of polarization of the laser beam impinging on the eye. This makes it possible to greatly reduce the scattered light from flares that constitutes the noise component, without producing much of a decrease in the scattered light from the cells that forms the signal component, thereby providing accurate measurement of cells even when there is a high level of flare components.

However, the result of cutting the flare component when the laser beam is thus polarized is that the scattered laser light, as viewed by the examiner via the observation section, virtually disappears, making it impossible to observe the state of the incident laser beam at the eye. For this reason the polarization is used only during measurements, while to make observation possible during the system alignment procedure prior to the measurement, the polarization of the laser beam is arranged to be perpendicular to the plane that includes the optical axes of the laser beam projection and light receiving sections.

Rayleigh scattering and Mie scattering will now be explained, with reference to light radiation. Rayleigh scattering is scattering that is produced by particles that are much smaller than the wavelength of the light and is not changed by changes in the light wavelength. If the volume of the scatterer is v, the permittivity is $=\epsilon$, the permittivity of the medium is $=\epsilon_0$, the wavelength of the incident light is $\lambda$ and the intensity is $I_0$, then at a distance r from the scatterer the intensity I of light with a scattering angle $\phi$ is given by the following equation.

$$I = I_0(2\pi^2 v^2/r^2\lambda^4)((\epsilon-\epsilon_0)/\epsilon_0)^2(1+\cos^2\phi)$$

Figures 7, 8, 9A, 9B:
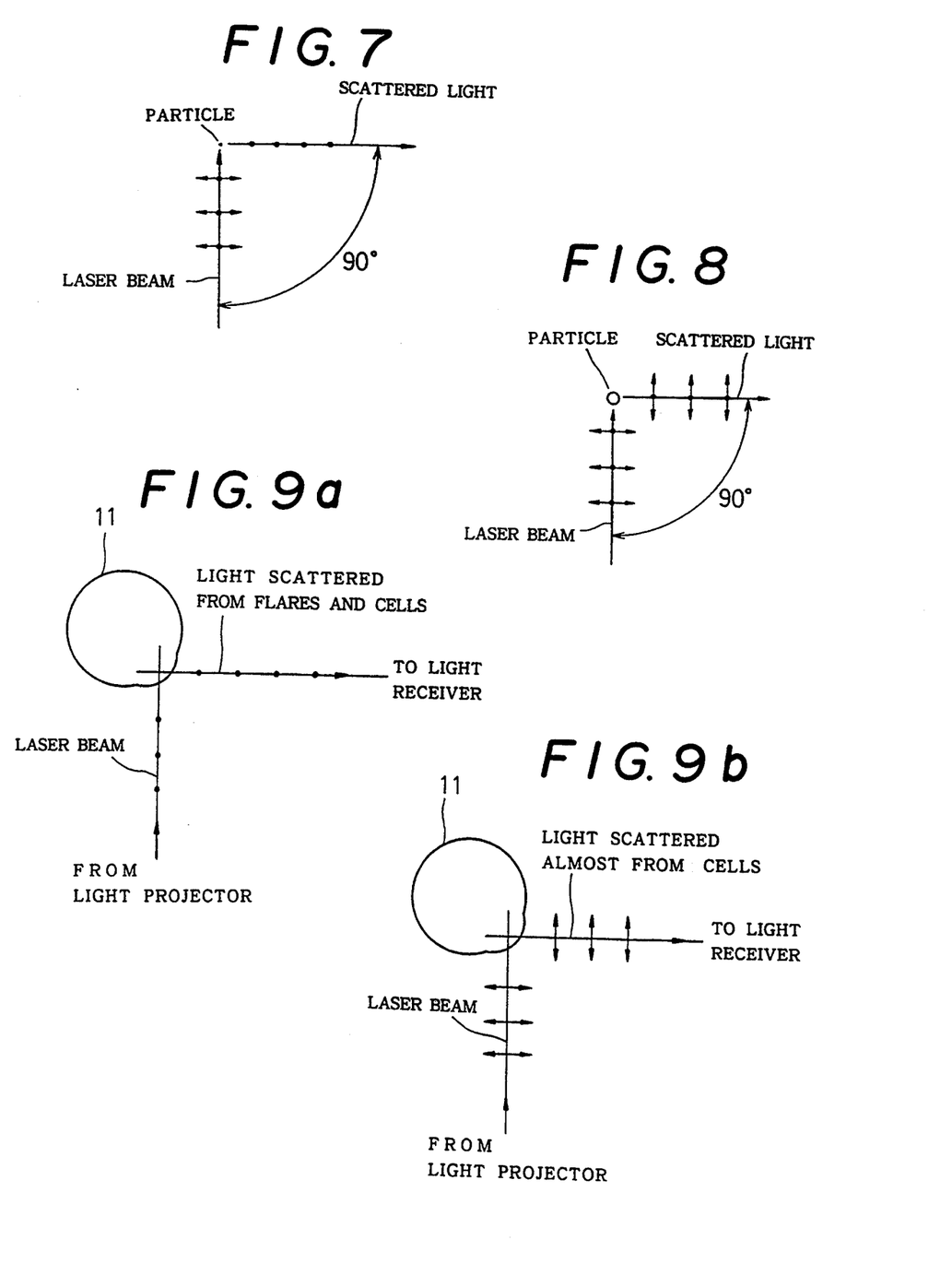
FIG. 7 is an explanatory diagram of Rayleigh scattering.
FIG. 8 is an explanatory diagram of Mie scattering.

With the first term, an electric field vector component perpendicular to a plane that includes incident and scattered light, and the second term a parallel component, particularly when the incident light beam is perpendicular (light scattering laterally at ninety degrees), the light polarization will be perfectly linear, as shown in FIG. 7. The dots in FIG. 7 indicate light polarized perpendicular to the drawing sheet, while the double-headed horizontal arrows indicate light polarized in the plane of the drawing sheet.

Scattering caused by particles such as flares that are much smaller than the light wavelength will be Rayleigh scattering. This means that, with respect to lateral scattering at ninety degrees arising from such small particles, only light with a polarization that is perpendicular to the plane that includes the optical axes of the laser beam projection and light receiving sections will be scattered, and light that is polarized in the direction of the plane will not be involved in the scattering.

Rayleigh scattering does not apply in the case of cells, which measure several tens of micrometers; instead, Mie scattering applies. (Owing to their extreme complexity Mie scattering equations have been omitted herein.) Based on Mie scattering theory, when the light is scattered laterally at right-angles the polarization direction of the incident beam has little effect. That means that whether the polarization of the incident beam is perpendicular or parallel to the plane that includes the laser beam projection and light receiving sections will have little effect on the intensity of the scattered light or on the polarization characteristics. This is illustrated by FIG. 8.

Further features of the invention, its nature and various advantages will become more apparent from a consideration of the accompanying drawings and following detailed description of the invention.

BRIEF DESCRIPTION OF THE DRAWINGS

FIG. 9 is an explanatory diagram of polarization states during system alignment and during measurement operations;

DETAILED DESCRIPTION OF THE PREFERRED EMBODIMENTS

Figure 1:
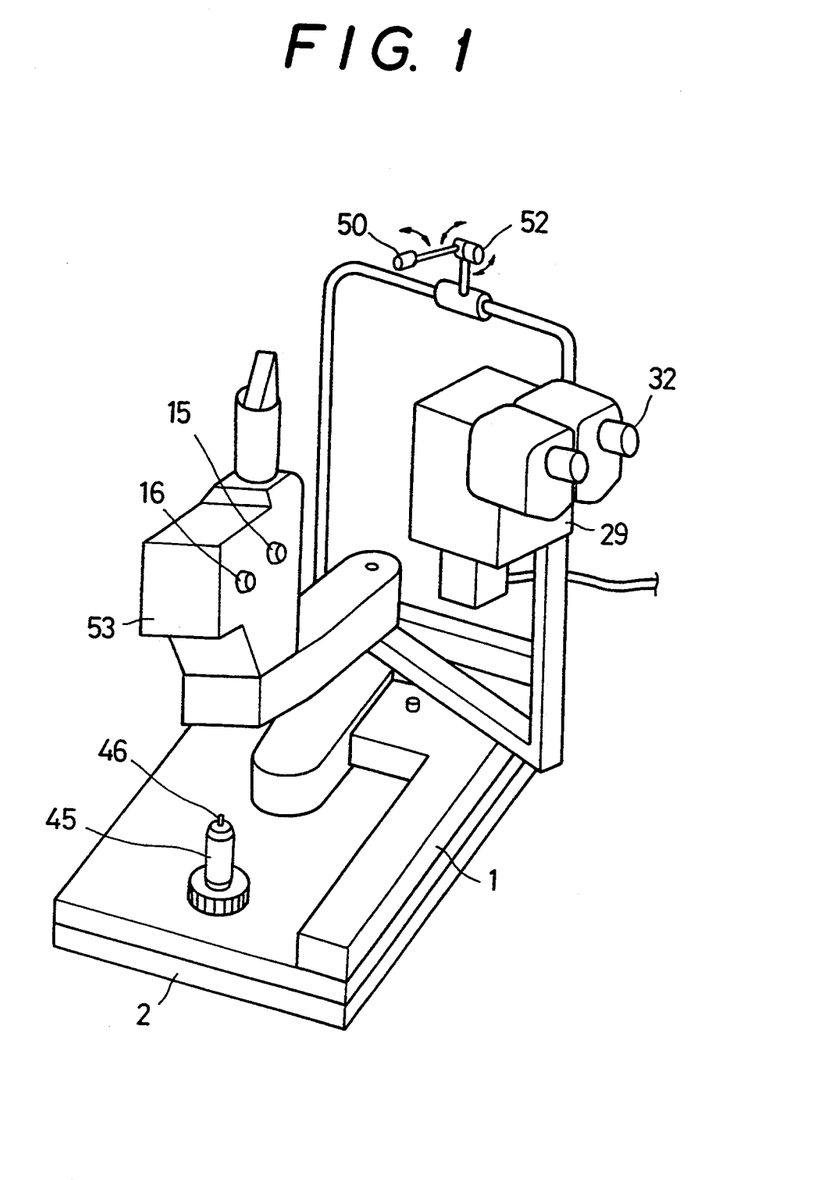
FIG. 1 is a perspective view of an embodiment of the ophthalmic measurement apparatus according to the present invention.

The invention will now be described in detail with reference to the drawings, starting with the arrangement of the ophthalmic measurement apparatus shown in FIGS. 1 to 3. In the drawings, reference numeral 1 denotes a laser light source such as a gas or semiconductor laser. In the case of a semiconductor laser, the source will include an optical system to shape the laser beam, and in the case of a random polarization gas laser, a polarizing plate. The laser light source 1 is disposed on a stand 2. The light from the laser light source 1 passes through a laser beam filter 3 to attenuate it, for example, and is directed by a vertical scanning mirror 4, a horizontal scanning mirror 4', prisms 5 and 6, a lens 7, a beam splitter 8, a condenser lens 9 and a prism 10 to converge at a prescribed point in the anterior chamber 11a of an eye under examination 11. Polarization varying means 1' varies a direction of polarization of the laser beam.

The laser beam projection section 53 is provided with a slit light source 12. Light from the slit light source 12 passes through a shutter 13 and a slit 14, and via the beam splitter 8, lens 9 and prism 10 forms a slit image in the anterior chamber 11a. This slit image illuminates the surrounding area, facilitating confirmation of the position of the point of converged light formed from the laser light source. The width and length of the slit 14 can be adjusted or changed by an adjusting knob 15 and a switching knob 16, respectively, which are shown in FIG. 1.

Figure 2:
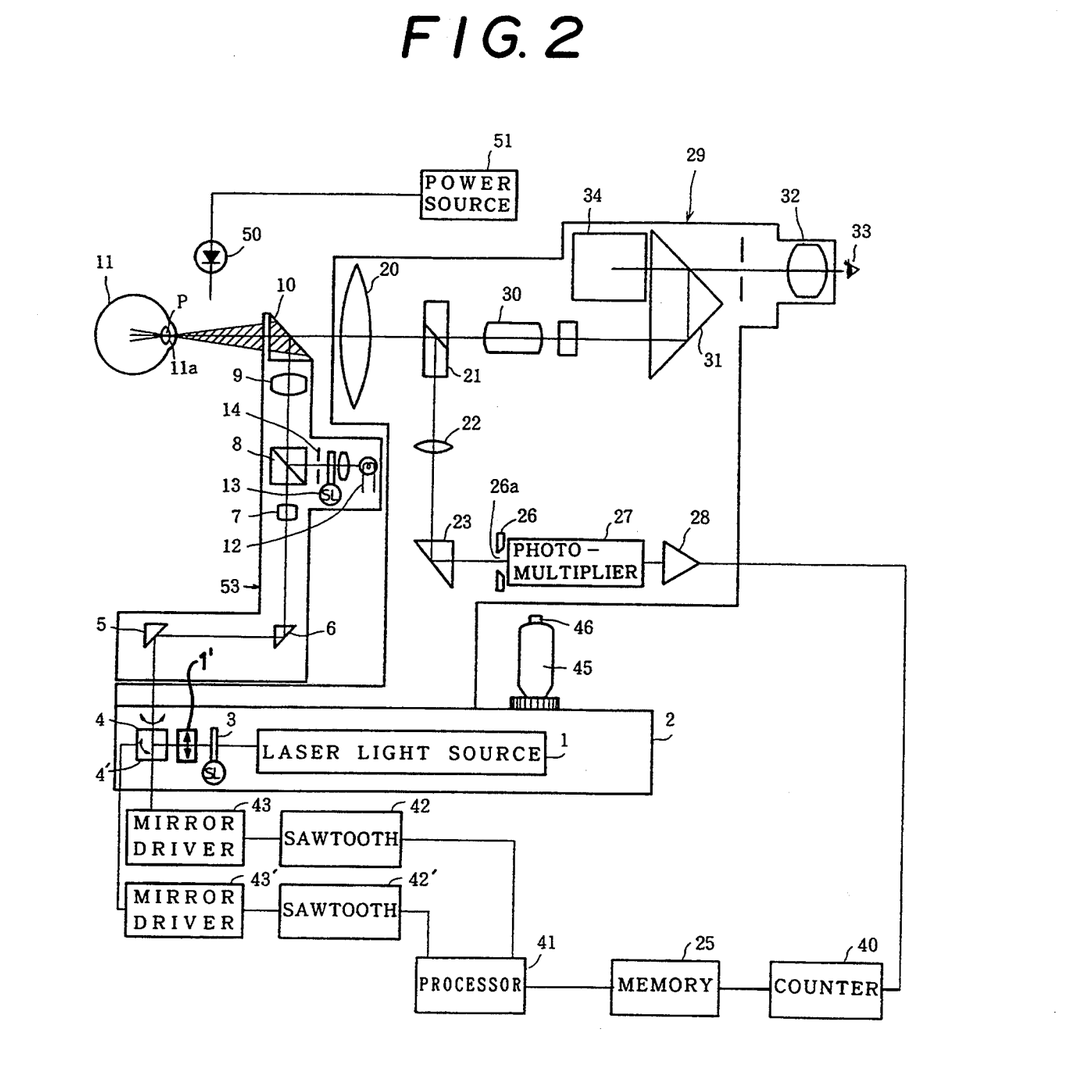
FIG. 2 is a diagram showing the overall configuration of the apparatus.

With reference to FIG. 2, a portion of the laser light scattered from the measurement point in the anterior chamber 11a passes through an objective lens 20 of a light receiving section 29 and is split by a beam splitter 21. One part of the light thus split passes via a variable-power lens 30 and prisms 31 and 34 to an eyepiece 32 by means of which an examiner 33 can observe the incidence of the laser beam. The other part of the scattered light split by the beam splitter 21 passes through a lens 22, a prism 23 and a mask 26 provided with a slit 26a and impinges on a photomultiplier 27 that constitutes the photosensor. The output from the photomultiplier 27 is passed via an amplifier 28 to a counter 40 where the intensity of the scattered light detected by the photomultiplier is measured as a count of the pulses per unit time period. The output of the counter 40, i.e. , the number of samplings or the total pulse count, is stored in a memory 25 that has an address for each unit time period. As described below, the data stored in the memory 25 is processed by an processor 41 that computes a count of the floating cells in the anterior chamber.

Figure 3:
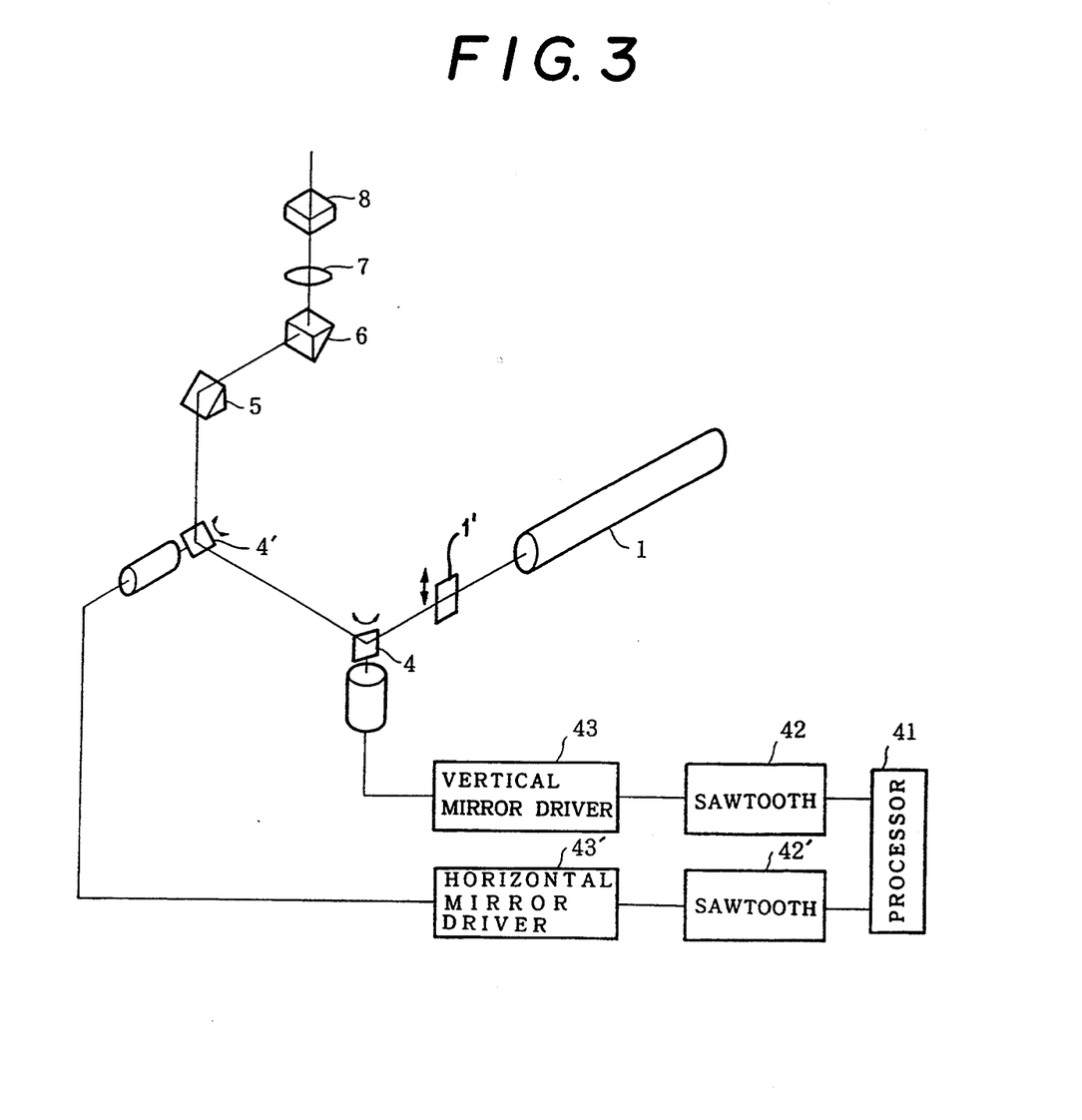
FIG. 3 is a diagram showing the arrangement of the laser beam optical scanning system.

With reference to the scanning system illustrated in FIG. 3, under the control of the processor 41 vertical and horizontal scanning mirror drive circuits 43 and 43' drive the vertical and horizontal scanning mirrors 4 and 4' in accordance with sawtooth scanning signals generated by sawtooth wave generators 42 and 42' to scan the point P of laser light vertically and horizontally within the anterior chamber.

In accordance with this invention, an eye fixation light 50 constituted of a light-emitting diode or the like powered by electricity supplied from a power source 51 is disposed at a position that permits the examiner to fix the patient's eye. The light selected for the eye fixation light 50 is of a different color than the light of the laser light source 1 . When the light from the laser light source is red a green light is selected, for example. A link mechanism 52 enables the eye fixation light 50 to be turned in the direction indicated by the arrow to adjust it to the optimum position with respect to the patient's eye.

The base 2 is equipped with an input means such as a joystick 45 equipped with a push-button 46. Pressing the push-button 46 enables the laser filter 3 and the slit light shutter 13 to be inserted into, and retracted from, the respective optical system. As described below, the push-button 46 is also used to rotate the polarization of the incident light by ninety degrees.

In the apparatus arranged as described above, the laser beam projection section 53 and light receiving section 29 are disposed so that the optical axes of the two sections (the axis of the laser beam entering the eye and the axis of the objective lens 20) form an angle of ninety degrees with respect to the eye 11. Light scattering at right-angles to the incident laser beam is used for the cell count.

The operation of the apparatus arranged thus will now be described. To carry out measurements, the slit light source 12 is activated and an image of the slit 14 is formed, via the beam splitter 8, lens 9 and prism 10, on a part of the anterior chamber 11a that includes the measurement point P. Also, the laser beam from the laser light source 1 is converged on the measurement point P via the above optical system. Via the observation optical system, the examiner uses the slit image to confirm the position of the point of converged laser light. Using the joystick 45 the optical system is aligned with the eye, and when this alignment has been done the pushbutton 46 is pressed.

As a result, the slit light shutter 13 is inserted into the light path of the slit light optical system, shutting off the slit light. Therefore, only laser light scattering from the measurement point P goes to the light receiving section 29 and passes to the photomultiplier 27 via the objective lens 20, beam splitter 21, lens 22, prism 23 and mask 26.

Figure 4A:
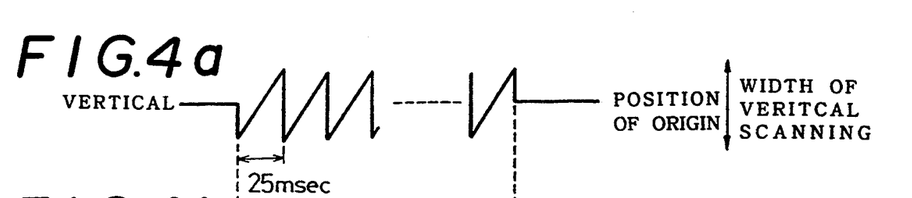
FIG. 4 shows laser beam scanning signal waveforms.
Figure 4B:
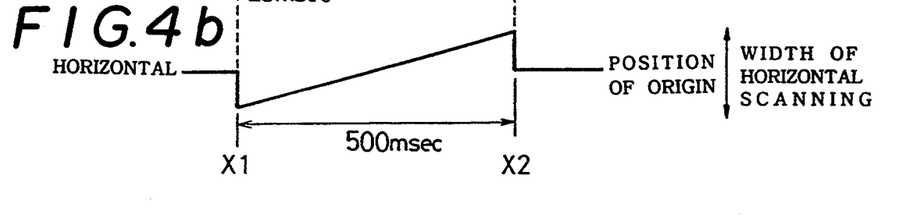
Figure 5:
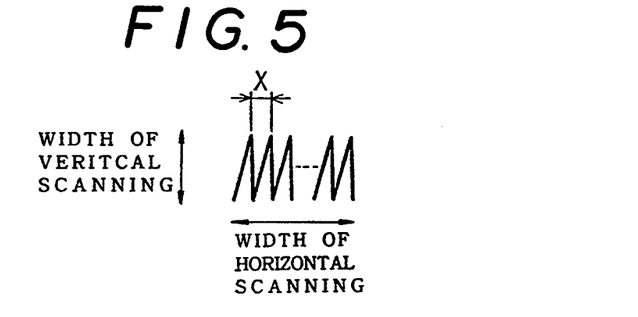
FIG. 5 is an explanatory diagram showing the path of the scanning laser beam.

Under the control of the processor 41, scanning is performed by the vertical and horizontal scanning mirrors 4 and 4' in accordance with sawtooth waveforms generated by sawtooth wave generators 42 and 42'. These waveforms are shown in FIG. 4a and FIG. 4b. In FIG. 4 X1 and X2 denote the measurement start and stop points, respectively. If Hf is the frequency of the horizontal scan signal, Vf the frequency of the vertical scan signal and N the number of vertical scans, then Hf=Vf/N. The vertical and horizontal scanning mirrors 4 and 4' are scanned in accordance with the signal waveforms, causing the laser beam to perform scanning with measurement point P at the center of the scan. FIG. 5 shows the path of the scanning light beam.

Thus, the photomultiplier 27 receives the scanning laser light scattering from the measurement point P and converts it into a series of pulses corresponding to the intensity. The number of pulses per unit time period are counted by a counter 40, and the count values are then stored in addresses provided in a memory 25 for each unit time period.

The apparatus of this invention is used to measure white blood cells, red blood cells, and chromocytes. Each of these three types of cell is at least several tens of micrometers in diameter. (While cortical tissue components and the like that form following IOL procedures are also counted, their larger size make such components readily distinguishable from anterior chamber floating cells.)

Figure 6:
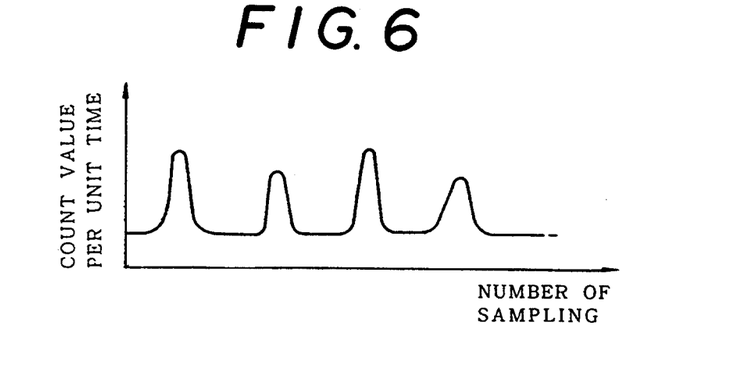
FIG. 6 is a curve showing peaks in the intensity of light scattered by cells.

When the laser beam scans across one of these cells it produces a peak in the intensity of the scattered light. Therefore, by setting the measurement unit time period (the unit time period used by the counter 40 to count pulses) to less than the time period required for the laser beam to traverse a cell, when the count values stored in the memory 25 are expressed in a time-series form the count values will only register an increase when the laser beam has scanned a cell, producing the type of waveform shown in FIG. 6 in which each peak has been produced by light scattered by a cell. The processor 41 is used to count the peaks and thereby establish the number of cells within the anterior chamber measurement space defined by the vertical and horizontal scanning of the laser beam.

Moreover, if the laser beam is moving at a constant velocity when it scans a cell and the beam diameter is known beforehand, the size of the cells can be calculated from the width of the peak (differentiation of cortical tissue is done at this point). To prevent the same particle being counted twice, the scanning waveform is given the sawtooth configuration shown in FIG. 5 and a vertical scanning rate is set at a value at which the peak-to-peak distance X is larger than the diameter of the laser beam.

During the measurement phase, the flare noise component in the scattered light is cut by polarizing the light projected into the eye by the laser beam projection section 53 so that the polarization is in a plane that includes the optical axis of the laser beam projection section 53 and optical axis of the light receiving section 29 (the axis of the laser beam projected into the eye and the axis of the objective lens 20). This configuration is illustrated by FIG. 9b, in which the double-headed horizontal arrows indicate the polarization direction of the incident laser beam.

With this polarization arrangement, with respect to light that is scattered substantially at ninety degrees to the side, particles such as flares that are much smaller than the wavelength of the light (Rayleigh scattering) will not participate in the scattering. On the other hand, as cells measure several tens of micrometers, in accordance with Mie scattering theory they will scatter the laser beam. By thus cutting the flare component in the scattered light, virtually all the scattered light received by the light receiving section 29 will be from cells, providing a good signal/noise ratio that produces accurate cell measurements.

However, cutting the flare component that constitutes a large portion of the scattered light leaves the light scattered by the cells, which, being intermittent and scattered, makes it impossible for an examiner viewing the eye 11 via the observation system to ascertain the path of the laser beam. This makes it difficult to carry out the system alignment procedure.

In view of this, in accordance with the present invention, during measurement operations the direction of laser beam polarization is changed to the setting shown in FIG. 9b, but during alignment operations and after completion of measurements the direction of laser beam polarization is changed so as to be perpendicular to the plane containing the optical axes of the laser beam projection section 53 and light receiving section 29, as shown in FIG. 9a. The dots in FIG. 9 indicate light polarization perpendicular to the drawing sheet. In this state, plasma proteins in the anterior chamber contribute to the scattered light and the flare component is not cut, giving the examiner a clear view of the path of the laser beam and enabling alignment to proceed without hindrance.

Thus, in accordance with this invention, the polarization direction of the laser beam projected at the eye that is perpendicular to the sheet of the FIG. 9 drawing during alignment operations is rotated by ninety degrees, into the horizontal plane. The arrangement for changing the polarization direction is shown in FIGS. 10 and 11.

Figure 10A:
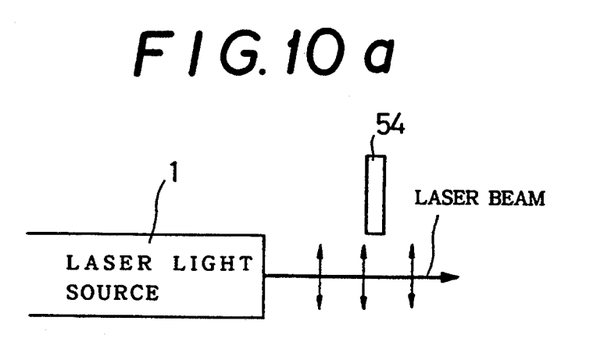
FIG. 10 is an explanatory diagram of the arrangement used to rotate the polarization of the laser beam.
Figure 10B:
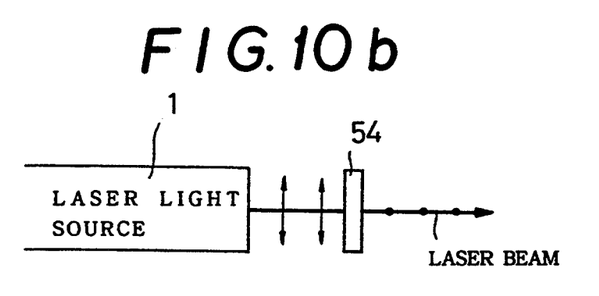

In the arrangement of FIG. 10 a half-wave plate 54 is used to change the polarization direction. FIG. 10a shows the state in which alignment is performed. In this state, the half-wave plate 54 is not inserted in the path of the laser beam emit ted by the laser light source 1, and the polarization direction of the laser beam is perpendicular to the plane that includes the optical axes of the laser beam projection section 53 and light receiving section 29. FIG. 10b shows the state used for measurements. Here the half-wave plate 54 is inserted into the path of the laser beam, rotating the polarization direction by ninety degrees, so it is within the plane that includes the optical axes of the laser beam projection section 53 and light receiving section 29. After the measuring operation is finished the halfwave plate 54 is retracted back to the position shown in FIG. 10a. This insertion and retraction of the halfwave plate 54 can be implemented anywhere within the laser beam projection section 53.

Figure 11A:
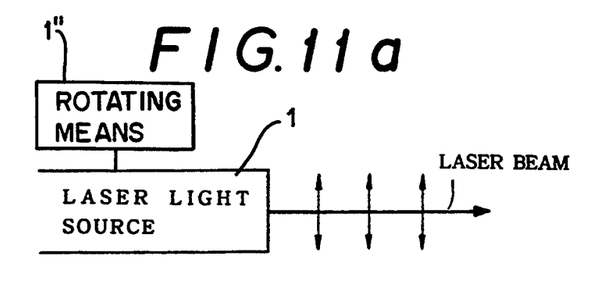
FIG. 11 is an explanatory diagram of another arrangement for rotating the polarization of the laser be am.
Figure 11B:
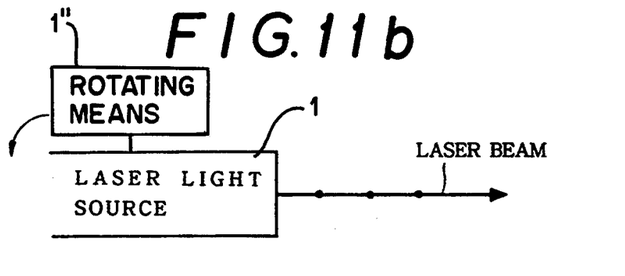

In the configuration of FIG. 11 the laser light source 1 is arranged so that it can be rotated about the axis of the laser beam. FIG. 11a shows the alignment operation setting in which the light source 1 has been rotated by rotating means 1" so that the polarization direction of the laser beam is perpendicular to the plane that includes the optical axes of the laser beam projection section 53 and light receiving section 29. FIG. 11b shows the measurement setting in which the light source 1 is rotated by ninety degrees to thereby rotate the polarization direction by ninety degrees. Again, after completing the measuring operation, the light source 1 is rotated back to the FIG. 11a setting. When a random polarization gas laser equipped with a polarizing plate is used as the light source 1, the gas laser and polarizing plate can be rotated together as a single assembly, or just the polarizing plate may be rotated.

The insertion and retraction of the half-wave plate 54 and the rotation of the light source 1 may be effected automatically by means of a solenoid or motor drive, operated by the push-button 46 of the joystick 45 in association with the insertion and retraction of the shutter 13.

While the above description states that it is preferable that the optical axes of the laser beam projection section 53 and light receiving section 29 form an angle of ninety degrees with respect to the eye, it is not necessary for it to be precisely ninety degrees; it may be approximately ninety degrees. Similarly, for the alignment and measurement operations the polarization direction of the laser beam from the laser beam projection section 53 need only be approximately perpendicular or parallel to the plane that includes the said optical axes.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmic measurement apparatus having an optical system for irradiating the interior of an eye with a beam of substantially visible-region laser light and using the light scattered from the interior of the eye to perform specific measurements, the apparatus comprising:
    a laser beam projection section for projecting into an eye a linearly polarized laser light beam emitted by a laser source;
    a light receiving section provided with a photosensor for detecting laser light scattering from within the eye, an angle of the optical axes formed by the laser beam projection section and light receiving section with respect to the eye to be examined being set to be substantially ninety degrees; and
    polarization varying means for varying a polarization direction of the laser beam from the laser beam projection section so that during alignment of the eye with the optical system of the apparatus the polarization direction is set substantially perpendicular to a plane that includes the eye, the optical axis of the laser beam projection section and the optical axis of light receiving section, and during measurement operations the polarization direction is set in a direction that is substantially in the plane.

2. An ophthalmic measurement apparatus according to claim 1; wherein the laser light source comprises one of a semiconductor laser, a linear polarization gas laser and a random polarization gas laser provided with a polarizing plate.

3. An ophthalmic measurement apparatus according to claim 1; wherein the polarization varying means includes a half-wave plate for varying the polarization direction of the laser light beam from the laser beam projection section by the retractable insertion of the half-wave plate into the laser beam light path in the laser beam projection section.

4. An ophthalmic measurement apparatus according to claim 1; wherein the polarization varying means includes rotating means for varying the polarization direction of the laser light beam from the laser beam projection section by rotating the laser light source.

5. An ophthalmic measurement apparatus according to claim 1; wherein the laser light source comprises a random polarization gas laser provided with a polarizing plate; and the polarization varying means includes means for varying the polarization direction of the laser light beam from the laser beam projection section by rotating the polarizing plate.

6. An ophthalmic measurement apparatus, comprising: laser beam projecting means for projecting a laser beam along a projection optical axis into an eye; light receiving means for receiving light scattered from the eye along a receiving optical axis for measurement of the scattered light, the laser beam projecting means and the light receiving means being arranged so that the projection optical axis is substantially perpendicular to the receiving optical axis; and polarization varying means for varying a direction of polarization of the laser beam so that a polarization direction during alignment operations of the ophthalmic measurement apparatus is different from a polarization direction during measurement operations by the ophthalmic measurement apparatus, wherein the polarization varying means includes means for varying the direction of polarization of the laser beam so that the polarization direction during the alignment operations is set substantially perpendicular to a plane that includes the eye, the projection optical axis and the light receiving optical axis, and the polarization direction during the measurement operations is set in a direction that is substantially in the plane.

7. An ophthalmic measurement apparatus, comprising: laser beam projecting means for projecting a laser beam along a projection optical axis into an eye; light receiving means for receiving light scattered from the eye along a receiving optical axis for measurement of the scattered light; and polarization varying means for varying a direction of polarization of the laser beam so that a polarization direction during alignment operations of the ophthalmic measurement apparatus is different from a polarization direction during measurement operations by the ophthalmic measurement apparatus, wherein the polarization varying means includes means for varying the direction of polarization of the laser beam so that the polarization direction during the alignment operations is set substantially perpendicular to a plane that includes the eye, the projection optical axis and the light receiving optical axis, and the polarization direction during the measurement operations is set in a direction that is substantially in the plane.

8. An ophthalmic measurement apparatus, comprising: laser beam projecting means for projecting a laser beam along a projection optical axis into an eye; light receiving means for receiving light scattered from the eye along a receiving optical axis for measurement of the scattered light; and polarization varying means for varying a direction of polarization of the laser beam so that a polarization direction during alignment operations of the ophthalmic measurement apparatus is different from a polarization direction during measurement operations by the ophthalmic measurement apparatus, wherein the polarization varying means includes means for varying the direction of polarization of the laser beam so that the polarization direction during the alignment operations is effective to include scattered light due to Rayleigh scattering received by the light receiving means, and during the measurement operations the polarization direction is effective to filter scattered light due to Rayleigh scattering received by the light receiving means.

9. An ophthalmic measurement apparatus, comprising: laser beam projecting means for projecting a laser beam along a projection optical axis into an eye; light receiving means for receiving light scattered from the eye along a receiving optical axis for measurement of the scattered light; and polarization varying means for varying a direction of polarization of the laser beam so that a polarization direction during alignment operations of the ophthalmic measurement apparatus is different from a polarization direction during measurement operations by the ophthalmic measurement apparatus, wherein the polarization varying means comprises inserting means for retractably inserting a half-wave plate into the laser beam path.

10. An ophthalmic measurement apparatus according to claim 9; wherein the inserting means is disposed between the laser beam projecting means and the eye.

* * * * *